US009023380B2

(12) United States Patent
Barrows et al.

(10) Patent No.: US 9,023,380 B2
(45) Date of Patent: May 5, 2015

(54) HAIR FOLLICLE GRAFT FROM TISSUE ENGINEERED SKIN

(75) Inventors: Thomas H. Barrows, Austell, GA (US); Preeti MacIntyre, Marietta, GA (US); Kenneth Justin Washenik, Los Angeles, CA (US)

(73) Assignee: Aderans Research Institute, Inc., Beverly Hills, CA (US)

( * ) Notice: Subject to any disclaimer, the term of this patent is extended or adjusted under 35 U.S.C. 154(b) by 5 days.

(21) Appl. No.: 12/729,700

(22) Filed: Mar. 23, 2010

(65) Prior Publication Data

US 2010/0178683 A1 Jul. 15, 2010

Related U.S. Application Data

(62) Division of application No. 11/562,703, filed on Nov. 22, 2006, now abandoned.

(60) Provisional application No. 60/738,931, filed on Nov. 22, 2005.

(51) Int. Cl.
| | | |
|---|---|---|
| *A61K 35/36* | (2006.01) | |
| *A61L 27/36* | (2006.01) | |
| *A61L 27/38* | (2006.01) | |
| *A61L 27/58* | (2006.01) | |
| *A61L 27/60* | (2006.01) | |

(52) U.S. Cl.
CPC .............. *A61K 35/36* (2013.01); *A61L 27/362* (2013.01); *A61L 27/3804* (2013.01); *A61L 27/3886* (2013.01); *A61L 27/58* (2013.01); *A61L 27/60* (2013.01); *A61L 2430/18* (2013.01)

(58) Field of Classification Search
CPC . A61K 38/00; A61K 47/48284; A61K 48/00; A61K 2300/00; A61K 35/12; A61K 35/30; A61K 38/17; A61K 31/155; A61K 31/426; A61K 31/4439; A61K 31/4965; A61K 38/04; A61K 38/28; A61K 45/06
See application file for complete search history.

(56) References Cited

U.S. PATENT DOCUMENTS

| | | | |
|---|---|---|---|
| 2,946,769 | A | 7/1960 | Rose et al. |
| 3,025,323 | A | 3/1962 | Rose et al. |
| 3,596,292 | A | 8/1971 | Erb et al. |
| 4,052,988 | A | 10/1977 | Doddi et al. |
| 4,104,195 | A | 8/1978 | Ley et al. |
| 4,209,607 | A | 6/1980 | Shalaby et al. |
| 4,226,243 | A | 10/1980 | Shalaby et al. |
| 4,343,931 | A | 8/1982 | Barrows |
| 4,384,061 | A | 5/1983 | Reiter et al. |
| 4,429,080 | A | 1/1984 | Casey et al. |
| 4,458,678 | A | 7/1984 | Yannas et al. |
| 4,505,266 | A | 3/1985 | Yannas et al. |
| 4,529,792 | A | 7/1985 | Barrows |
| 4,604,097 | A | 8/1986 | Graves, Jr. et al. |
| 4,643,734 | A | 2/1987 | Lin |
| 4,719,917 | A | 1/1988 | Barrows et al. |
| 4,851,521 | A | 7/1989 | della Valle et al. |
| 4,919,664 | A | 4/1990 | Oliver et al. |
| 4,947,840 | A | 8/1990 | Yannas et al. |
| 5,061,284 | A | 10/1991 | Laghi |
| 5,091,173 | A | 2/1992 | Buultjens et al. |
| 5,133,739 | A | 7/1992 | Bezwada et al. |
| 5,141,522 | A | 8/1992 | Landi |
| 5,147,400 | A | 9/1992 | Kaplan et al. |
| 5,194,473 | A | 3/1993 | Shinoda et al. |
| 5,198,507 | A | 3/1993 | Kohn et al. |
| 5,286,837 | A | 2/1994 | Barrows et al. |
| 5,376,542 | A | 12/1994 | Schlegal |
| 5,403,347 | A | 4/1995 | Roby et al. |
| 5,423,778 | A | 6/1995 | Eriksson et al. |
| 5,486,593 | A | 1/1996 | Tang et al. |
| 5,502,092 | A | 3/1996 | Barrows et al. |
| 5,514,378 | A | 5/1996 | Mikos et al. |
| 5,522,841 | A | 6/1996 | Roby et al. |
| 5,545,208 | A | 8/1996 | Wolff et al. |
| 5,556,783 | A | 9/1996 | Lavker et al. |
| 5,578,046 | A | 11/1996 | Liu et al. |
| 5,599,552 | A | 2/1997 | Dunn et al. |
| 5,611,811 | A | 3/1997 | Goldberg |
| 5,661,132 | A | 8/1997 | Eriksson et al. |
| 5,667,961 | A | 9/1997 | Bernard et al. |
| 5,674,286 | A | 10/1997 | D'Alessio et al. |
| 5,677,355 | A | 10/1997 | Shalaby et al. |
| 5,690,961 | A | 11/1997 | Nguyen |
| 5,697,901 | A | 12/1997 | Eriksson |

(Continued)

FOREIGN PATENT DOCUMENTS

| | | |
|---|---|---|
| CA | 2140090 | 8/1995 |
| CA | 2199918 | 9/1997 |

(Continued)

OTHER PUBLICATIONS

Oliver, R.F. "The induction of hair follicle formation in the adult hooded rat by vibrissa dermal papillae", J. Embroyl. exp. Morph., vol. 23, 1, pp. 219-236. Published Feb. 1970.*
Arase, et al., "Co-culture of human hair follicles and dermal papillae in a collagen matrix", *J. Dermatol.*, 17:667-676 (1990).
Arase, et al., "Culture of dispersed hair follicle cells from plucked out hairs without a feeder layer", *Tokushima J. Exp. Med.*, 36:87-95 (1989).
Atala, "Tissue engineering and regenerative medicine: concepts for clinical application.", *Rejuvenation Res.*, 7:15.31 (2004).
Auger, et al., "A truly new approach for tissue engineering: the LOEX self-assembly technique", Ernst Schering Res. Found. Workshop, 35:73-88 (2002).
Barrows, et al., "Tissue Engineered Human Hair: Preliminary Clinical Results", TE2002: International Workshop on Tissue Engineering, St. Gallen, Switzerland (2002).
Bieberich, et al., "Differential expression of the Hox 3.1 gene in adult mouse skin", Ann NY Acad Sci, 642:346-354 (1991).
Bioglass Technology, U.S. Biomaterials Corporation, http://www.usbiomat.com/bioglass.html (Dec. 28, 2000).

(Continued)

*Primary Examiner* — Audrea Buckley
(74) *Attorney, Agent, or Firm* — Pabst Patent Group LLP

(57) ABSTRACT

The present invention provides a hair graft comprising (a) tissue engineered skin comprising a tissue engineered epidermal layer, a tissue engineered dermal layer, and hair follicle progenitor cells and (b) a scaffold. The invention also provides methods of making and using the hair grafts of the present invention.

17 Claims, No Drawings

(56) References Cited

U.S. PATENT DOCUMENTS

| | | | |
|---|---|---|---|
| 5,697,976 A | 12/1997 | Chesterfield et al. | |
| 5,712,169 A | 1/1998 | Bernard et al. | |
| 5,721,049 A | 2/1998 | Marcolongo et al. | |
| 5,723,508 A | 3/1998 | Healey et al. | |
| 5,756,094 A | 5/1998 | Lavker et al. | |
| 5,767,152 A | 6/1998 | Nielsen et al. | |
| 5,770,417 A | 6/1998 | Vacanti et al. | |
| 5,817,120 A | 10/1998 | Rassman | |
| 5,847,012 A | 12/1998 | Shalaby et al. | |
| 5,851,831 A | 12/1998 | Inamatsu | |
| 5,891,426 A | 4/1999 | Jarrousse et al. | |
| 5,898,040 A | 4/1999 | Shalaby et al. | |
| 5,919,893 A | 7/1999 | Roby et al. | |
| 5,939,323 A | 8/1999 | Valentini et al. | |
| 5,945,115 A | 8/1999 | Dunn et al. | |
| 5,968,546 A | 10/1999 | Baur et al. | |
| 5,980,888 A | 11/1999 | Dimoudis | |
| 5,989,279 A | 11/1999 | Rassman | |
| 5,993,374 A | 11/1999 | Kick | |
| 5,997,468 A | 12/1999 | Wolff et al. | |
| 5,997,568 A | 12/1999 | Liu | |
| 6,001,378 A | 12/1999 | Desjonqueres | |
| 6,027,744 A | 2/2000 | Vacanti et al. | |
| 6,031,148 A | 2/2000 | Hayes et al. | |
| 6,051,750 A | 4/2000 | Bell | |
| 6,093,200 A | 7/2000 | Liu et al. | |
| 6,120,788 A | 9/2000 | Barrows | |
| 6,147,135 A | 11/2000 | Yuan et al. | |
| 6,159,950 A | 12/2000 | Crystal et al. | |
| 6,333,029 B1 | 12/2001 | Vyakarnam et al. | |
| 6,350,284 B1 | 2/2002 | Tormala et al. | |
| 6,365,172 B1 | 4/2002 | Barrows | |
| 6,383,220 B1 | 5/2002 | van Blitterswijk et al. | |
| 6,423,252 B1 | 7/2002 | Chun et al. | |
| 6,474,344 B2 | 11/2002 | Yamada | |
| 6,497,875 B1 * | 12/2002 | Sorrell et al. | 424/93.7 |
| 6,503,539 B2 | 1/2003 | Gestrelius et al. | |
| 6,511,748 B1 | 1/2003 | Barrows | |
| 6,548,058 B1 | 4/2003 | Hunziker et al. | |
| 6,569,143 B2 | 5/2003 | Alachas et al. | |
| 6,613,798 B1 | 9/2003 | Porter et al. | |
| 6,639,051 B2 | 10/2003 | Wang | |
| 6,673,603 B2 | 1/2004 | Baetge et al. | |
| 6,699,287 B2 | 3/2004 | Son et al. | |
| 6,730,513 B1 | 5/2004 | Hunziker et al. | |
| 6,773,713 B2 | 8/2004 | Bonassar et al. | |
| 6,878,383 B2 | 4/2005 | Boss, Jr. et al. | |
| 6,884,427 B1 | 4/2005 | Barrows | |
| 7,160,726 B2 | 1/2007 | Mansbridge | |
| 7,163,679 B1 | 1/2007 | Kishimoto | |
| 7,198,641 B2 | 4/2007 | Barrows | |
| 2002/0049426 A1 | 4/2002 | Butler et al. | |
| 2002/0090725 A1 | 7/2002 | Simpson et al. | |
| 2002/0172705 A1 * | 11/2002 | Murphy et al. | 424/422 |
| 2002/0193740 A1 | 12/2002 | Alachas et al. | |
| 2002/0193778 A1 | 12/2002 | Alachas et al. | |
| 2003/0009113 A1 | 1/2003 | Olson | |
| 2003/0049839 A1 | 3/2003 | Romero-Ortega et al. | |
| 2003/0072784 A1 | 4/2003 | Williams | |
| 2003/0077311 A1 | 4/2003 | Vyakarnam et al. | |
| 2003/0077823 A1 | 4/2003 | Li et al. | |
| 2003/0134099 A1 | 7/2003 | Barrows | |
| 2003/0147831 A1 | 8/2003 | Marko | |
| 2003/0161815 A1 | 8/2003 | Wolowacz et al. | |
| 2003/0166274 A1 | 9/2003 | Hewitt et al. | |
| 2003/0195625 A1 | 10/2003 | Garcia Castro et al. | |
| 2003/0198646 A1 | 10/2003 | Stenn | |
| 2003/0203003 A1 | 10/2003 | Nelson et al. | |
| 2003/0235813 A1 | 12/2003 | Luyten et al. | |
| 2004/0033598 A1 | 2/2004 | Vacanti et al. | |
| 2004/0039438 A1 | 2/2004 | Alt | |
| 2004/0057937 A1 | 3/2004 | Jahoda et al. | |
| 2004/0068284 A1 | 4/2004 | Barrows | |
| 2004/0220589 A1 | 11/2004 | Feller | |
| 2005/0089512 A1 | 4/2005 | Schlotmann et al. | |
| 2005/0147652 A1 | 7/2005 | Atkins et al. | |
| 2005/0191748 A1 | 9/2005 | Barrows | |
| 2005/0214344 A1 | 9/2005 | Barrows | |
| 2005/0233450 A1 | 10/2005 | Goetinck et al. | |
| 2005/0272150 A1 | 12/2005 | Teumer et al. | |
| 2006/0057126 A1 | 3/2006 | Tankovich | |
| 2006/0062770 A1 | 3/2006 | Zheng et al. | |
| 2007/0092496 A1 | 4/2007 | Zheng et al. | |
| 2007/0122387 A1 | 5/2007 | Cochran et al. | |
| 2007/0148138 A1 | 6/2007 | Barrows et al. | |
| 2007/0233038 A1 | 10/2007 | Pruitt et al. | |

FOREIGN PATENT DOCUMENTS

| | | |
|---|---|---|
| CN | 15944554 | 3/2005 |
| EP | 0405656 | 1/1991 |
| EP | 0236014 | 7/1991 |
| EP | 0971679 | 1/2000 |
| EP | 1002859 | 5/2000 |
| EP | 1083874 | 3/2001 |
| EP | 1089704 | 4/2001 |
| EP | 1098626 | 5/2001 |
| EP | 0845963 | 9/2003 |
| EP | 1437042 | 7/2004 |
| EP | 1612265 | 1/2006 |
| EP | 1337624 | 9/2006 |
| EP | 1702632 | 9/2006 |
| JP | 3273028 | 12/1991 |
| JP | 4108444 | 4/1992 |
| JP | 7048769 | 2/1995 |
| JP | 10136977 | 5/1998 |
| JP | 2000229889 | 8/2000 |
| JP | 2001302520 | 10/2001 |
| JP | 2002145701 | 5/2002 |
| JP | 2003070466 | 3/2003 |
| JP | 2003189849 | 7/2003 |
| JP | 2003235990 | 8/2003 |
| JP | 2003238421 | 8/2003 |
| JP | 2003328229 | 11/2003 |
| WO | WO 98/44027 | 10/1998 |
| WO | WO 98/47471 | 10/1998 |
| WO | WO 99/01034 | 1/1999 |
| WO | WO 99/34750 | 7/1999 |
| WO | WO 99/62491 | 12/1999 |
| WO | WO 00/03749 | 1/2000 |
| WO | WO 00/29553 | 5/2000 |
| WO | WO 00/45736 | 10/2000 |
| WO | WO 00/62829 | 10/2000 |
| WO | WO 01/58413 | 8/2001 |
| WO | WO 01/66472 | 9/2001 |
| WO | WO 01/70132 | 9/2001 |
| WO | WO 01/70289 | 9/2001 |
| WO | WO 01/70290 | 9/2001 |
| WO | WO 01/70291 | 9/2001 |
| WO | 0174164 | 10/2001 |
| WO | WO 02/15952 | 4/2002 |
| WO | WO 02/060396 | 8/2002 |
| WO | WO 03/022043 | 3/2003 |
| WO | WO 03/055990 | 7/2003 |
| WO | WO 03/057152 | 7/2003 |
| WO | WO 03/068248 | 8/2003 |
| WO | WO 03/088935 | 10/2003 |
| WO | WO 03/104443 | 12/2003 |
| WO | WO 2004/044188 | 5/2004 |
| WO | WO 2005/018731 | 3/2005 |
| WO | WO 2005/033302 | 4/2005 |
| WO | WO 2005/053763 | 6/2005 |
| WO | WO 2005/007221 | 10/2005 |
| WO | WO 2006/020958 | 2/2006 |
| WO | WO 2006/057542 | 6/2006 |
| WO | WO 2007/047707 | 4/2007 |
| WO | WO 2007/062386 | 5/2007 |
| WO | WO 2007/062387 | 5/2007 |
| WO | WO 2007/092929 | 8/2007 |

OTHER PUBLICATIONS

Blanpain, et al., "Self-renewal, multipotency, and the existence of two cell populations within an epithelial stem cell niche", *Cell*, 118:635-648 (2004).

(56) References Cited

OTHER PUBLICATIONS

Bucala, et al., "Circulating fibrocytes define a new leukocyte subpopulation that mediates tissue repair", *Mol. Med.*, 1:71-81 (1994).
Chang, et al., "Sculpting skin appendages out of epidermal layers via temporally and spatially regulated apoptotic events", *J. Invest. Dermatol.*, 122:1348-1355 (2004).
Chiang, et al., "Essential Role for Sonic hedgehog during Hair Follicle Morphogenesis", *Dev. Biol.*, 205:1-9 (1999).
Christian, et al., "Microarray analysis of human, rat, and mouse dermal papilla and connective sheath cells reveals multiple factors with potential for hair follicle growth regulations", *J. Invest. Derm.*, 119(1):292 (2002).
Claudinot, et al., "Long-term renewal of hair follicles from clonogenic multipotent stem cells", *PNAS*, 102:14677-14682 (2005).
Cohen, "The transplantation of individual rat and guinea-pig whisker papillae", *J. Embryol. Exp. Morphol.*, 9:117-127 (1961).
Cotsarelis, et al., "Label-retaining cells reside in the bulge area of pilosebaceous unit. Implications for follicular stem cells, hair cycle and skin carcinogenesis", *Cell*, 61:1329-1337 (1990).
Cotsarelis, et al., "Towards a molecular understanding of hair loss and its treatment", *Trends Mol. Med.*, 7:293-301 (2001).
Deleens, et al., "A new generation of thermoplastic elastomers the polyether block amide (PEBA)", SPIE 39$^{th}$ Ann. Tech. Conf., Boston, MA (1981).
Dlugosz, "The Hedgehog and the hair follicle: a growing relationship", *J. Clin. Invest.*, 104:851-853 (1999).
Domashenko, et al., "Efficient delivery of transgenes to human hair follicle progenitor cells using topical lipoplex", *Nat. Biotech.*, 18:420-423 (2000).
Dry, "The coat of the mouse (*Mus musculus*)", *J. Genetics* (Bateson and Punnett, eds.), 287-340 (1926).
Du Cros, et al., "Association of versican with dermal matrices and its potential role in hair follicle development and cycling", *J. Invest. Dermatol.*, 105:426-431 (1995).
Dyce, et al., "Stem cells with multilineage potential derived from porcine skin", *Biochem. Biophys. Res. Commun.*, 316:651-658 (2004).
Ebling, "The biology of hair", *Dermatol. Clin.*, 5(31:467-481 (1987).
Evans, et al., "In vivo evaluation of poly(L-lacatic acid) porous conduits for peripheral nerve regeneration", *Biomaterials*, 20:1109-1115 (1999).
Favier, et al., "Localization of members of the notch system and the differentiation of vibrissa hair follicles: receptors, ligands, and fring modulators", *Dev. Dyn.*, 218(3):426-437 (2000).
Ferraris, et al., "Adult epidermal keratinocytes are endowed with pilosebaceous forming abilities", *Int. J. Dev. Biol.*, 41:491-498 (1997).
Fieser and Fieser, "Reagents for Organic Synthesis", John Wiley and Sons, Inc., 704-706 (1967).
Foitzek, et al., "Prolactin and its receptor are expressed in murine hair follicle epithelium, show hair cycle-dependant expression, and induce catagen", *Am. J. Path.*, 162(5):1611-1621 (2003).
Foitzek, et al., "Control of murine hair follicle regression (catagen) by TGF-B1 in vitro", *The FASEB Journal*, 14:752-760 (2000).
Fujie, et al., "The chemotactic effect of a dermal papilla cell-derived factor on outer root sheath cells", *J. Dermatol. Sci.*, 25(3):206-212 (2001).
Gharzi, et al., "Plasticity of hair follicle dermal cells in wound healing and induction", *Exp. Dermatol.*, 12:126-136 (2003).
Gho, et al., "Hair transplantation of plucked hair biopsies", *Dermatol. Surg.*, 27(10):913 (2001).
Gho, et al., "To Multiply or Not to Multiply, That is the Question . . . ", Abstract of presentation at the International Society of Hair Restoration Surgeons, New York City Conference (2003).
Hardy, "The development of mouse hair in vitro with some observations on pigmentation", *J. Anat.*, 83:364-384 (1949).
Hardy, "The secret life of the hair follicle", *Trends in Genetics*, 8:55-61 (1992).
Hashimoto, et al., "Histological examination of human hair follicles grafted onto severe combined immunodeficient (SCID) mice", *Hair Research for the Next Millenium* (Van Neste and Randall, eds.), Elsevier Science BV: Amsterdam, 141-145 (1896).
Hoffmann, et al., "Aromatase and oxidative 3alpha-hydroxysteroid dehydrogenase are present in human hair follicles and regulate intrafollicular DHT levels", *J. Invest. Derm.*, 119(11:292 (2002).
Hoffmann, et al., "Steroid sulfatase in the human hair follicle concentrates in the dermal papillae", *J. Invest. Dermatol.*, 117:1342-1348 (2001).
Hoffmann, et al., "17alpha-estradiol induces aromatase activity in intact human anagen hair follicles ex vivo", *Exp. Dermatol.*, 11:376-380 (2002).
Horch, et al., "Tissue engineering of cultured skin substitutes", *J. Cell Mol. Med.*, 9(3):592-608 (2005).
Horne, et al., "Whisker growth induced by implantation of cultured vibrissa dermal papilla cells in the adult rat", *J. Embryol, Exp. Morphol.*, 97:111-124 (1986).
Hu, et al., "Polypeptide resurfacing method improves fibroblast's adhesion to hyaluronan strands.", *J. Biomed. Mate. Res.*, 47(1):79-84 (1999).
Ibraheem, et al., "Growth and viability of secondary hair follicles of the Angora goat cultured in vitro", *J. Anatomy*, 182(2):231-238 (1993).
Iguchi, et al., "Human follicular papilla cells carry out nonadipose tissue production of leptin", *J. Invest. Dermatol.*, 117:1349-1356 (2001).
Ihara, et al., "Formation of hair follicles from a single-cell suspension of embryonic rat skin by a two-step procedure in vitro", *Cell Tissue Res.*, 266:65-73 (1991).
Inaba, "Chapter 16. The Question of Hair Regeneration.", *Human Body Odor, Etiology Treatment and Related Factors*, Springer-Verlag: Tokyo, 235-260.
Inamatsu, et al., "Establishment of rat dermal papilla cell lines that sustain the potency to induce hair follicles from afollicular skin", *J. Invest. Dermatol.*, 111(5):767-775 (1998).
Inui, et al., "Androgen-inducible TGF-beta1 from balding dermal papilla cells inhibits epithelial growth: a clue to understand paradoxical effects of androgen on human hair growth", *FASEB J.*, 16(14):1967-1969 (2002).
Jahoda and Oliver, "The growth of vibrissa dermal papilla cells in vitro", *Br. J. Dermatol.*, 105:623-627 (1981).
Jahoda and Reynolds, "Hair follicle dermal sheath cells: unsung participants in wound healing", *Lancet*, 358:1445-1448 (2001).
Jahoda, "Induction of follicle formation and hair growth by vibrissa dermal papillae implanted into rat ear wounds: vibrissa-type fibres are specified", *Development*, 115(4):1103-1109 (1992).
Jahoda, et al., "Induction of Hair Growth in Ear Wounds by Cultured Dermal Papilla Cells", *J. Invest. Dermatol.*, 101(4):584-590 (1993).
Jahoda, et al., "Human Hair follicle regeneration following amputation and grafting into the nude mouse", *J. Invest. Dermatol.*, 107(6):804-807 (1996).
Jahoda, et al., "Induction of hair growth by implantation of cultured dermal papilla cells", *Nature*, 311(5986):560-562 (1984).
Jahoda, et al., "Dermal-Epidermal Interactions, Adult Follicle-Derived Cell Populations and Hair Growth", *Dermatologic Clinics*, 14(4):573-583 (1996).
Jahoda, "Hair follicle dermal cells differentiate into adipogenic and osteogenic lineages", *Exp. Dermatol.*, 12:849-859 (2003).
Jahoda, et al., "Dermal-epidermal interactions—follicle-derived cell populations in the study of hair-growth mechanisms", *J. Invest. Dermatol.*, 101(1):33S-38S (1993).
Jahoda, et al., "Trans-species hair growth induction by human hair follicle dermal papillae", *Exp. Dermatol.*, 10:229-237 (2001).
Jiang, et al., "Pluripotency of mesenchymal stem cells derived from adult marrow", *Nature*, 418:41-49 (2002).
Kamimura, et al., "Primary mouse keratinocyte cultures contain hair follicle progenitor cells with multiple differentiation potential", *J. Invest. Dermatol.*, 109(4):534-540 (1997).
Katayama, et al., "Synthesis of Alternating Polyamide Esters by Melt and Solution Polycondensations of N,N'-Di(6-hydroxycaproyl)

(56) References Cited

OTHER PUBLICATIONS dimines and N-6-Hydroxycaproyl Aminoalcohol with Terephthalic and Adipic Dimethyl Esters and Dichlorides", *J. Applied Polymer Sci.*, 20:975-994 (1976).
Kim, et al., "Interferon beta secreted from human hair dermal papilla cells inhibits the growth outer root sheath cells cultured in vitro", *Biochem. Biophys. Res. Commun.*, 290:1133-1138 (2002).
Kishimoto, et al., "Role of versican in anagen hair induction during hair cycle", *J. Invest. Dermatol.*, 119(1):287 (2002).
Kishimoto, et al., "Selective activation of the versican promoter by epithelial-mesenchymal interactions during hair follicle development", *Proc. Natl. Acad. Sci. U.S.A.*, 96(13):7336-7341 (1999).
Kishimoto, et al., "Wnt signaling maintains the hair-inducing activity of the dermal papilla", *Genes Dev.*, 14(10):1181-1185 (2000).
Kruluger, et al., "Reorganization of hair follicles in human skin organ culture induced by cultured human follicle-derived cells", *Exp. Dermatol.*, 14(8):580-585 (2005).
Kulessa, et al., "Inhibition of Bmp signaling affects growth and differentiation in the anagen hair follicle", *EMBO J.*, 19(24):6664-6674 (2000).
Lako, et al., "Hair follicle dermal cells repopulate the mouse hematopoietic system", *J. Cell Sci.*, 115:3967-3974 (2002).
Lavker, et al., "Hair follicle stem cells: Their location, role in hair cycle, and involvement in skin tumor formation", *J. Invest, Dermatol.*, 101(1):16S-26S (1993).
Layer, et al., "Of layers and spheres: the reaggregate approach in tissue engineering", *Trends Neurosci.*, 25:131-134 (2002).
Lee, "Tissue-engineered human living skin substitutes: development and clinical application", *Yonsei Med. J.*, 41(6):774-779 (2000).
Li, et al., "Roles of TGFbeta signaling in epidermal/appendage development", *Cytokine & Growth Factor Reviews*, 14(2):99-111 (2003).
Lichti, et al., "In vivo regulation of murine hair growth: insights from grafting defined cell populations onto nude mice", *J. Invest. Dermatol.*, 101(1 Suppl):124S-129S (1993).
Lichti, et al., "Hair follicle development and hair growth from defined cell populations grandted onto nude mice", *J. Invest. Dermatol.*, 104(5):43S-44S (1995).
Lin, et al., "Activation of the notch pathway in the hair cortex leads to aberrant differentiation of the adjacent hair-shaft layers", *Development*, 127:2421-2432 (2000).
Lindner, et al., "Involvement of hepatocyte growth factor/scatter factor and met receptor signal hair follicle morphogenesis and cycling", *FASEB J.*, 14(2):319-332 (2000).
Luo, et al., "Modification of Natural Polymers: Hyaluronic Acid", *Methods of Tissue Engineering* (Atala and Lanza, eds.), Academic Press, 539-553 (2002).
Lyle, et al., "The C8/1448 monoclonal antibody recognizes cytokeratin 15 and defines the location of human hair follicle stem cells", *J. Cell. Sci.*, 111:3179-3188 (1998).
Ma, et al., "Synthetic nano-scale fibrous extracellular matrix", *J. Biomed. Mater. Res.*, 46(1):60-72 (1999).
Magerl, et al., "Simple and rapid method to isolate and culture follicular papillae from human hair follicles", *Exp. Dermatol.*, 11:381-385 (2002).
Malkinson and Keane, "Hair Matrix Cell Kinetics: A Selective Review", *Intl. J. Dermatol.*, 17(71:536-551 (1978).
Matsuzaki, et al., "Localization and migration of follicular melanocyt precursors in mouse vibrissae during hair cycle", *Zoological Sci.*, 19(12):1450 (2000).
Mayorov, et al., "B2 elements present in the human genome", *Mamm. Genome*, 11:177-179 (2000).
McElwee, et al., "Cultured Peribulbar Dermal Sheath Cells Can Induce Hair Follicle Development and Contribute to the Dermal Sheath and Dermal Papilla", *J. Invest. Dermatol.*, 121:1267-1275 (2003).
Messenger, "The control of hair growth: an overview", *J. Invest. Dermatol.*, 101(1 Suppl):4S-9S (1993).
Messenger, "Hair Follicle Tissue Culture", *Br. J. Dermatol.*, 113:639-640 (1985).

Messenger, "The culture of dermal papilla cells from human hair follicles", *Br. J. Dermatol.*, 110:685-689 (1984).
Michel, et al., "Characterization of a new tissue-engineered human skin equivalent with hair", *In Vitro Cell. Dev. Biol. Anim.*, 35(6):318-326 (1999).
Misago, et al., "Proliferation and differentiation of organoid hair follicle cells co-cultured with fat cells in collagen gel matrix culture. ", *British J. Dermatology*, 139:40-48 (1998).
Miyashita, et al., "Characterization of hair follicles induced in implanted, cultured rat keratinocyte sheets", *Exp. Dermatol.*, 13(8):491-498 (2004).
Moore, et al., "Extracellular matrix molecules and follicle morphogenesis in ovine skin", *Reprod. Fertil. Dev.*, 13(2-3):143-149 (2001).
Morris, et al., "Capturing and profiling adult hair follicle stem cells", *Nat. Biotech.*, 22:1-7 (2004).
Nakamura, et al., "Control of pelage hair follicle development and cycling by complex interaction between follistatin and activin", *FASEB J.*, 17:497-499 (2003).
Nam and Park, "Porous biodegradable polymeric scaffolds prepared by thermally induced phase separation", *J. Blamed. Mater. Res.*, 47(1):8-17 (1999).
Nixon, et al., "Regulation of prolactin receptor expression in ovine skin in relation to circulatory prolactin and wool follicle growth status", *J. Endocrinol.*, 172:605-614 (2002).
Nixon, et al., "Transforming Growth fator-alpha Immunoreactivity During Induced Hair Follicle Growth Cycles in Sheep and Ferrets", *J. Histochem. Cytochem.*, 44:377-387 (1996).
Oliver, "Local interactions in mammalian hair growth", *Mammalian Hair Growth*, 199-210 (1980).
Oliver and Jahoda, "The Dermal Papilla and Maintenance of Hair Growth", *Dermal Papilla and Hair Growth*, Cambridge University Press: Cambridge, 51-67 (1989).
Oliver, "The dermal papilla and the development of hair growth", *J. Soc. Cosmet, Chem.*, 22:741-755 (1971).
Oliver, et al., "Whisker growth after removal of the dermal papilla and lengths of follicle in the hooded rat", *J. Embryol. Exp. Morphol.*, 15(3):331-347 (1966).
Oliver, "Histological studies of whisker regeneration in the hooded rat", *J. Embryol. Exp, Morphol.*, 16(2):231-244 (1966).
Oliver, "The experimental induction of whisker growth in the hooded rat by implantation of dermal papillae", *J. Embryol, Exp. Morphol.*, 18(1):43-51 (1967).
Oliver, "The induction of hair follicle formation in the adult hooded rat by vibrissa dermal papillae", *J. Embryol. Exp. Morphol.*, 23(1):219-236 (1970).
Oliver, "Ectopic regeneration of whiskers in the hooded rat from implanted lengths of vibrissa follicle wall", *J. Embryol. Exp. Morphol.*, 17:27-34 (1967).
Osada, et al., "Characterization of vibrissa germinative cells: transition of cell types", *Exp. Dermatol.*, 10:430-437 (2001).
Oshima, et al., "Morphogenesis and renewal of hair follicles from adult multipotent stem cells", *Cell*, 104:233-245 (2001).
Ota, et al., "Fibroblast growth factor 5 inhibits hair growth by blocking dermal papilla cell activation", *Biochem. Biophys. Res. Comm.*, 290(1):169-176 (2002).
Patrick, et al., eds. "Prospectus of Tissue Engineering", *Frontiers in Tissue Engineering*, Elsevier Science, Inc.: New York, 3-11 (1998).
Paus, et al., "A comprehensive guide for the recognition and classification of distinct stages of hair follicle morphogenesis", *J. Invest. Dermatol.*, 113:523-532 (1999).
Paus, et al., "Telogen skin contains an inhibitor of hair growth", *Br. J. Dermatol.*, 122:777-784 (1990).
Philpott, et al., "Effects of Insulin and Insulin-like Growth Factors on Cultured Human Hair Follicles: IGF-I at Physiologic Concentrations is an Important Regulator of Hair Follicle Growth In Vitro", *J. Invest. Derm.*, 120:857-861 (1994).
Philpott, et al., "In vitro maintenance of isolated hair follicles: current status and future development", *Exp. Dermatol.*, 8(4):317-319 (1999).

(56) References Cited

OTHER PUBLICATIONS

Pisansarakit, et al., "Cultivation of mesenchymal cells derived from the skin and hair follicles of the sheep the involvement of peptide factors in growth regulation", *Arch Dermatol. Res.*, 183(5):321-327 (1991).
Pispa and Thesleff, "Mechanisms of ectodermal organogenesis", *Dev. Biol.*, 262:195-205 (2003).
Pouliot, et al., "Reconstructed human skin produced in vitro and grafted on athymic mice", *Transplantation*, 73(11):1751-1757 (2002).
Price, "Treatment of Hair Loss", *N. Eng. J. Med.*, 341:964-973 (1999).
Prouty, et al., "Fibroblast-dependent induction of a murine skin lesion similar to human nevus sebaceous of jadassohn", *Lab. Invest.*, 6(2)79-189 (1997).
Prouty, et al., "Fibroblast-dependent induction of a murine skin lesion with similarity to human common blue nevus", *Am. J. Pathol.*, 148(6):1871-1885 (1996).
Raposio, et al., "Follicular bisection in hair transplantation surgery: an in vitro model", *Plastic and Reconstructive Surgery*, 221-226 (1998).
Rassman, et al., "Rapid fire hair implanter carousel", *Dermatologic Surgery*, 24:623-627 (1998).
Ratner, et al., "Biamaterials: where we have been and where we are going", *Anna. Rev. Biomed. Eng.*, 6:41-75 (2004).
Regineili, et al., "Digit tip regeneration correlates with regions of Mxs1 (Hox 7) expression in fetal and newborn mice", *Development*, 121:1065-1076 (1995).
Remmler, et al., "Use of injectable cultured human fibroblasts for percutaneous tissue implantation", *Arch Otolaryngol. Head Neck Surg.*, 115:837-844 (1989).
Rendl, et al., "Molecular dissection of mesenchymal-epithelial interactions in the hair follicle", *PLOS Biol.*, 3(11):1910-1924 (2005).
Reynolds and Jahoda, "Inductive Properties of Hair Follicle Cells", *Annals New York Academy of Sciences*, 624:226-242 (1991).
Reynolds and Jahoda, "Hair fibre progenitor: developmental status and interactive potential", *Dev. Biol.*, 4:241-250 (1993).
Reynolds, et al., "Human Hair Follical Germinative Epidermal Cell Culture", *J. Invest. Dermatol.*, 101(4):634-638 (1992).
Reynolds and Jahoda, "Hair follicle reconstructive in vitro", *J. Dermatol. Sci.*, 7 Suppl:S84-S97 (1994).
Reynolds and Jahoda, "Cultured dermal papilla cells induce follicle formation and hair growth by transdifferentiation of an adult epidermis", *Development*, 115:587-593 (1992).
Reynolds, et al., "Trans-gender induction of hair follicles", *Nature*, 402:33-34 (1999).
Robinson, et al., "Hair cycle stage of the mouse vibrissa follicle determines subsequent fiber growth and follicle behavior in vitro", *J. Invest. Dermatol.*, 108:495-500 (1997).
Rogers, et al., "Cultivation of murine hair follicles as organoids in a collagen matrix", *J. Invest. Dermatol.*, 89(4):369-379 (1987).
Sato, et al., "Induction of the hair growth phase in postnatal mice by localized transient expression of sonic hedgehog", *J. Clin. Invest.*, 104:855-864 (1999).
Sawaya, et al., "Effects of finasteride on apoptosis and regulation of the human hair cycle", *J. Cutan. Med. Surg.*, 6(1):1-9 (2002).
Saywell, et al., "Cell proliferation during fibre growth initiation in ferret hair follicles", *Proceedings of the New Zealand Society of Animal Production*, 52:299-302 (1992).
Schmidt-Ullrich, et al., "Molecular principles of hair follicle induction and morphogenesis", *Bioessays*, 27:247-261 (2005).
Scwarz, et al., "Epithelial-mesenchymal interactions are linked to neovascularization", *Amer. J. Respir. Cell. Mol. Biol.*, 30:784-792 (2004).
Soma, et al., "Involvement of transforming growth factor-beta2 in catagen induction during human hair cycle", *J. Invest. Dermatol.*, 118:993-997 (2002).
Stenn and Paus, "Controls of Hair Follicle Cycling", *Physiological Reviews*, 81(1):449-494 (2001).
Stenn, et al., "Bioengineering the hair follicle: fringe benefits of stem cell technology", *Curr. Opin. Biotech.*, 16:1-5 (2005).
Stenn, et al., "Re-epithelialization", *The Molecular and Cellular Biology of Wound Repair* (Clark, ed.), Plenum Press, 321-335 (1988).
Stenn, "Induction of hair follicle growth", *J. Invest. Dermatol.*, 96(5):80S (1991).
Stenn, et al., "Hair follicle growth controls", *Dermatol. Clinics*, 14:543-558 (1996).
Stenn, et al., "Growth of the Hair Follicle: A Cycling and Regenerating Biological System", *The Molecular Basis of Epithelial Appendage Morphogenesis* (Chuong, ed.), Landes Publ.: Austin, TX, 111-130 (1998).
Stenn, et al., "Bioengineering the hair follicle: fringe benefits of stem cell technology", *Curr. Opin. Biotech.*, 16(5):493-497 (2005).
Sundberg, et al., "Asebia-2J(Scd1(ab2J)): a new allele and a model for scarring alopecia", *Am. J. Path.*, 156:2067-2075 (2000).
Thornton, et al., "Ability to culture dermal papilla cells from red deer (*Cervus elaphus*) hair follicle differing hormonal responses in vivo offers a new model for studying the control follicle biology", *J. Experimental Zoology*, 275(6):452-458 (1996).
Tomihata and Ikada, "Crosslinking of hyaluronic acid with water-soluble carbodiimide", *J. Biomed. Mater. Res.*, 37:243-251 (1997).
Trempus, et al., "Enrichment for living murine keratinocytes from the hair follicle bulge with the cell surface marker CD34", *J. Invest. Dermatol.*, 120:501-511 (2003).
Warren, et al., "Improved method for the isolation and cultivation of human scalp dermal papilla cells", *J. Invest. Dermatol.*, 98(5):693-699 (1992).
Watson, et al., "Sheep vibrissa dermal papillae induce hair follicle formation in heterotypic skin equivalents", *Br. J. Dermatol.*, 131:827-835 (1994).
Weinberg, et al., "Reconstruction of hair follicle development in vivo: determination of follicle formation, hair growth, and hair quality by dermal cells", *J. Invest. Dermatol.*, 100(3):229-235 (1993).
Widelitz, et al., "Molecular Histology in Skin Appendage Morphogenesis", *Microsc. Res. Tech.*, 38:452-465 (1997).
Widlitz and Chuong, "Early events in skin appendage formation: Induction of epithelial placodes and condensation of dermal mesenchyme", *J. Invest. Dermatol. Sympos. Proc.*, 4(3):302-306 (1999).
Williams, et al., "Isolation and culture of follicular papillae from murine vibrissae: an introductory approach", *Br. J. Dermatol.*, 130:290-297 (1994).
Wilson, et al., "Cells within the bulge region of mouse hair follicle transiently proliferate during early gloom: heterogeneity and functional differences of various hair cycles", *Differentiation*, 55(2):127-136 (1994).
Worst, et al., "Reformation of organized epidermal structure by transplantation of suspensions and cultures of epidermal and dermal cells", *Cell. Tissue. Res.*, 225(1):65-77 (1982).
Xing and Kobayashi, "Ability of Transplanted Cultured Epithelium to Respond to Dermal Papillae", *Tissue Engineering*, 7:535-544 (2001).
Yagita, "CD95 ligand graft rejection", *Nature*, 379:682-683 (1996).
Yang, et al., "Cell sheet engineering: recreating tissue without biodegradable scaffolds", *Biometer.*, 26(33):6415-6422 (2005).
Yang, et al., "Upper-Human Hair Follicle Contains a Subpopulation of Keratinocytes with Superior In Vitro Proliferative Potential", *J. Invest. Dermatol.*, 101(5):652-659 (2005).
Yano, et al., "Control of hair growth and follicle size by VEGF-mediated angiogenesis", *J. Clin. Invest.*, 107(4):409-417 (2001).
Yano, et al., "Thrombospondin-1 plays a critical role in the induction of hair follicle involution vascular regression during the catagen phase", *J. Invest. Dermatol.*, 120:14-19 (2003).
Yuspa, et al., "Regulation of hair follicle development: An in vitro model for hair follicle invasion of dermis and associated connective tissue remodeling", *J. Invest. Dermatol.*, 101(1):27S-32S (1993).
Zheng, et al., "Organogenesis from dissociated cells: generation of mature cycling hair follicles from skin-derived cells", *J. Invest. Dermatol.*, 124:867-876 (2005).
Itami, et al., "Role of androgen in mesenchymal epithelia interactions in human hair follicle" , J. Investig Dermatol Symp Proc., 10(3):209-11 (2005).
Matsuzaki, et al., "Role of hair papilla cells on induction and regeneration processes of hair follicles" , Wound Repair Regen., 6(6):524-30 (1998).

\* cited by examiner

HAIR FOLLICLE GRAFT FROM TISSUE ENGINEERED SKIN

CROSS REFERENCE TO RELATED APPLICATIONS

This application is a divisional of U.S. Ser. No. 11/562,703 filed Nov. 22, 2006 now abandoned, which claims the benefit of and priority to U.S. Provisional Application No. 60/738,931, filed Nov. 22, 2005, which is incorporated by referenced herein.

BACKGROUND

Hair loss may occur due to a variety of conditions and may affect anyone: men, women and children. Hair loss conditions include, but are not limited to, alopecia capitis totalis, i.e., loss of all scalp hair, alopecia universalis, i.e., loss of hair over the whole body, alopecia greata, i.e., patchy hair loss, and androgenetic alopecia, i.e., male pattern baldness. Medications are available to treat alopecia including minoxidil, finasteride, corticosteroids and anthralin. However, any new hair growth resulting from the medication generally stops upon discontinuation of the medication.

More aggressive hair restoration methods include hair transplants and scalp reduction surgery. Hair transplantation entails excision of a full-thickness strip of scalp tissue from the back of the head, dissecting the excised scalp tissue into hundreds of "follicular unit grafts", each containing from one to several hairs, and implanting the grafts into recipient sites created by making stab wounds in the bald sections of the scalp. Hair transplantation creates no new hair follicles and often not all of the explanted follicles successfully transplant. Scalp reduction surgery, which is becoming less popular, aims to surgically reduce the area of bald skin on subject's head. Both hair transplantation and scalp reduction surgery are expensive and may be painful. Moreover, both carry possible risks of infection and scarring.

It is well known that specific cells within the hair follicle, including epidermal stem cells and dermal papilla cells, have the capacity to induce follicle neogenesis. Attempts have been made to exploit the inductive capabilities of these cells, including injecting dermal papilla cells directly into the skin and implanting plucked hairs carrying epithelial cells having various proliferative and differentiative characteristics. Previous attempts at producing follicle neogenesis have failed to produce reliable, reproducible and cosmetically satisfactory results.

SUMMARY

In one embodiment, the present invention provides a hair graft comprising (a) tissue engineered skin comprising a tissue engineered epidermal layer, a tissue engineered dermal layer, and hair follicle progenitor cells and (b) a scaffold, wherein the scaffold is at least 2 millimeters thick.

In other embodiments, the invention provides methods of making and using the hair grafts of the present invention.

DETAILED DESCRIPTION

The present invention provides a novel graft for hair follicle formation comprising a layer of tissue engineered skin comprising a tissue engineered epidermal layer and a tissue engineered dermal layer and hair follicle progenitor cells on a bioabsorbable scaffold. Tissue engineered skin by itself is suitable for transplantation. However, it is extremely thin and difficult to manipulate using traditional hair graft techniques. The scaffold provides rigidity and stability to the tissue engineered skin so that the graft can be easily manipulated.

The tissue engineered skin may be prepared by any suitable method known to one skilled in the art. For example, human neonatal foreskin tissue can be used as a source of human dermal fibroblasts that are multiplied in culture and seeded onto a scaffold such as collagen gel to provide a tissue engineered dermal layer. Epidermal keratinocytes can be obtained from the same neonatal tissue or, alternatively, obtained from plucked hair follicles. A tissue engineered epidermal layer can be produced from plucked hair follicles as disclosed in U.S. Pat. Nos. 6,730,513, 6,673,603, 6,548,058, 5,968,546, and references cited therein, the teachings of which are incorporated by reference herein. The tissue engineered dermal layer and tissue engineered epidermal layer can be separately prepared and then assembled into tissue engineered skin with hair follicle progenitor cells dispersed therein, suitably sandwiched between the two assembled layers. The tissue engineered dermal and epidermal layers can be prepared without the use of a scaffold, for example by the method described by Pouliot, et al. in *Transplantation,* 2002 Jun. 15; 73(11):1751-7, and references cited therein, the teachings of which are incorporated by reference herein.

In one embodiment, the tissue engineered skin containing follicle progenitor cells is placed on a bioabsorbable scaffold of suitable thickness to form a construct and is cultured further in vitro until the living skin construct is firmly attached to the bioabsorbable scaffold. In another embodiment, the tissue engineered dermal layer is placed on a bioabsorbable scaffold. Hair follicle progenitor cells are placed on the dermal layer and then a tissue engineered epidermal layer is placed on top of the hair follicle progenitor cells to form a construct. Alternatively, the tissue engineered dermal layer can be formed on a bioabsorbable scaffold. Hair follicle progenitor cells are then placed on the dermal layer and a tissue engineered epidermal layer is placed on top of the hair follicle progenitor cells.

In another embodiment, the tissue engineered dermal layer can be prepared on a bilayer scaffold comprising a bottom layer of an artificial skin implant, such as the Integra Dermal Regeneration Template™ (Integra NeuroSciences, Plainsboro, N.J.) in which the silicon rubber layer has been removed and replaced with a top layer of collagen. The collagen coating is then seeded with dermal fibroblasts and cultured in vitro.

Suitably, the hair follicle progenitor cells may be mesenchymal stem cells, dermal papilla cells, dermal sheath cells, follicular epidermal stem cells, also known as "bulge" cells, or any combinations thereof. Suitably, the progenitor cells are aggregated or clumped together prior to placement in the tissue engineered skin. The size of the aggregates is suitably from about 10 to about 500 microns, or about 20 to about 200 microns or about 30 to about 60 microns.

The construct comprising the tissue engineered skin containing hair follicle progenitor cells and the bioabsorbable scaffold is then cut into grafts suitable for implantation into the skin. The construct is cut such that grafts with the epidermal layer facing one direction and the scaffold facing the opposite direction are formed. The size and shape of the cuts is optimized such that little or no construct is wasted and the longest dimension is perpendicular to the tissue layers. The grafts are suitably cut into a size that is equivalent to a single hair graft, a follicular unit graft or modified follicular unit graft. Typically, these grafts are about 1 to about 9 square millimeters in surface area, or about 2 to about 8 square millimeters, or about 4 to about 6 square millimeters. The thickness is suitably about the same as the thickness of scalp skin. Suitably, the graft is at least about 2 millimeters thick, or at least about 5 millimeters thick, or at least about 8 millimeters thick, or at least about 10 millimeters thick. As used herein, "thick" is used to describe the height of the graft, i.e. the z-axis of the graft.

The bioabsorbable scaffold is a non-cytotoxic structure or substance that is capable of containing or supporting living cells and holding them in a desired configuration for a period of time. The term "bioabsorbable" refers to any material the human body can break down into non-toxic by-products that are excreted from the body or metabolized therein. Suitable bioabsorbable materials for the scaffold include, but are not limited to, poly(lactic acid), poly(glycolic acid), poly(trimethylene carbonate), poly(dimethyltrimethylene carbonate), poly(amino acids)s, tyrosine-derived poly(carbonates)s, poly(carbonates)s, poly(caprolactone), poly(para-dioxanone), poly(esters)s, poly(ester-amides)s, poly(anhydrides)s, poly(ortho esters)s, collagen, gelatin, serum albumin, proteins, polysaccharides, mucopolysaccharides, carbohydrates, glycosaminoglycans, poly(ethylene glycols)s, poly(propylene glycols)s, poly(acrylate esters)s, poly(methacrylate esters)s, poly(vinyl alcohol), hyaluronic acid, chondroitin sulfate, heparin, dermatan sulfate, versican, copolymers, blends and mixtures of polymers, and oligomers containing bioabsorbable linkages.

For example, hyaluronic acid may be converted into an insoluble crosslinked material ("HAX") by treatment with a condensing agent, suitably 1-ethyl-3-(3-dimethylaminopropyl) carbodiimide ("EDC"). Alternatively, hyaluronic acid may be converted into an insoluble material by esterification, e.g., the benzyl ester of hyaluronic acid, and used to prepare the bioabsorbable scaffold. Suitably, trans-esterification crosslinked HAX is used because the resultant product is then converted back into soluble hyaluronic acid upon hydrolysis of the ester linkages. Hydrolysis of the ester linkages takes place within a few days in vivo. Various cross linking agents may be employed including, but not limited to, aliphatic diamines, diaminoacid esters such as alkyl esters of lysine, and amine-terminated polyethylene glycol).

Various molecular moieties may be associated with the bioabsorbable scaffold using, for example, surface modifications, graft polymerization, copolymerization of bioabsorbable materials or blending of at least one moiety and the bioabsorbable material(s) used in forming the bioabsorbable scaffold. Moieties that may be associated with the bioabsorbable scaffold include, but are not limited to, growth factors, cell attachment binding site moieties, angiogenesis factors, cell signaling molecules, other small molecules, e.g., drugs that enhance hair follicle regrowth such as monoxidil, glycoproteins, e.g., chondroitin sulfate, dermatan sulfate, and versican, other bioactive molecules or combinations thereof.

Association of at least one moiety with the bioabsorbable scaffold may suitably be advantageous for improved association between various types of hair follicle progenitor cells and/or improved cell function, cell aggregation or cell initiation of the follicle neogenesis process. Attached moieties, such as growth factors and angiogenesis factors, may be released during the degradation of the bioabsorbable scaffold and encourage blood vessel growth into the newly formed follicle. Attachment of higher molecular weight moieties, such as proteins, glycoproteins, and other biopolymers, such as collagen, laminin, and fibronectin, may be physically or electro-statically bound to the bioabsorbable scaffold to suitably provide greater physical integrity, cell attachment capacity, or bioactivity.

For example, association of bioactive molecules to the HAX structure suitably enhances the performance of the resultant scaffold, e.g., association of peptides containing the cell attachment domain sequence of amino acids Arg-Gly-Asp (RGD) may be used to enhance dermal papilla cell attachment to the scaffold.

The term "growth factor" refers to a naturally occurring protein capable of stimulating cellular proliferation and cellular differentiation. Growth factors are important for regulating a variety of cellular processes. Well-known growth factors suitable for use in the present invention include, but are not limited to, granulocyte-colony stimulating factor ("G-CSF"), granulocyte-macrophage colony stimulating factor ("GM-CSF"), nerve growth factor ("NGF"), neutrophins, platelet-derived growth factor ("PDGF"), erythropoietin ("EPO"), thrombopoietin ("TPO"), myostatin ("GDF-8"), growth differentiation factor-9 ("GDF9"), basic fibroblast growth factor ("bFGF" or "FGF2"), epidermal growth factor ("EGF"), placenta derived growth factor ("PLGDF"), and hepatocyte growth factor ("HGF").

Similarly, the term "angiogenesis factor" refers to a naturally occurring protein capable of stimulating angiogenesis. Suitable angiogenesis factors for the present invention include, but are not limited to, vascular endothelial growth factor ("VEGF"), endothelial cell stimulating angiogenesis factor ("ESAF") and any nonmitogenic angiogenesis factors present in wound fluid.

The term "cell attachment binding site moiety" refers to a protein that plays a role in cell-cell/cell-matrix interaction and cellular communications. Examples of suitable cell attachment binding site moieties include, but are not limited to, integrins, cadherins, cell adhesion molecules ("CAMs"), selectins, fibronectin and fibronectin fragments including synthetic fribronectin-mimetic binding sites such as the RGD amino acid sequence.

The term "cell signaling molecule" refers to a chemical involved in transmitting information between cells. Such molecules are released from the cell sending the signal by crossing over the gap between cells, interacting with receptors in another cell, and triggering a response in that cell. Cell signaling molecules naturally are part of a complex system of communication that governs basic cellular activities and coordinates cell actions. These include nitric oxide and various steroids.

The term "bioactive molecule" refers to any molecule that has pharmacological activity that is beneficial to hair follicle neogenesis and survival. Suitable bioactive molecules may include, but are not limited to, cell signaling agonists or antagonists.

In another embodiment of the present invention, the grafts are manually implanted in wounds created in the desired implantation site using techniques similar to those used with traditional follicular units. Alternatively, the hair graft and bioabsorbable scaffold combination may be implanted using the "stick and place" method of grafting. In the "stick and place" method, the skin is pierced with the sharp point of a hollow needle or tube that also serves as a container for the bioabsorbable scaffold ensheathed hair graft. The tube is then inserted into the wound and withdrawn against a push rod that prevents the graft from coming out of the tube and ensures correct placement of the graft. A modification of the "stick and place" method may use a tool such as the Choi implanter, which requires breaking the skin with a pointed instrument prior to inserting the tube and depositing the implant.

In a further embodiment of the present invention, the scaffold used to provide sufficient thickness to the tissue engineered follicle progenitor cell-seeded skin is the same scaffold as that used to create the tissue engineered dermal layer. Thus, the scaffold for this purpose may have an isotropic structure such that the surface is designed for accepting dermal fibroblasts and facilitating their multiplication and maturation into a tissue engineered dermal layer, whereas the bulk of the scaffold is a porous structure designed to allow rapid tissue ingrowth upon implantation. A suitable scaffold for this purpose can be prepared, for example, by coating the surface of a highly porous synthetic or cross-linked biopolymer scaffold to be seeded with dermal cells with a layer of collagen or other suitable biopolymer or cell-compatible substance. After the dermal skin cells are confluent with the surface of the scaffold the hair follicle progenitor cells or aggregates thereof are placed on top of the dermal tissue equivalent and allowed to attach. A tissue engineered epidermal layer is placed on top of the hair follicle progenitor cells to complete formation of the construct. The construct is cultured further while submerged in culture medium and then brought to the air interface to allow the epidermis to mature to complete the formation of tissue engineered skin, as is standard practice in the art of producing tissue engineered skin.

In a further embodiment of the present invention, the scaffold that provides thickness to the tissue engineered follicle progenitor cell-seeded skin can also serve as a vehicle to add other cells to the graft that provide a beneficial effect. These cells may include, for example, fat cells, pre-adipocytes, endothelial cells, and bone marrow cells. These additional cells suitably are autologous cells obtained from the patient in need of the hair graft. Thus, the tissue engineered skin components of the graft can be obtained from neonatoal foreskin, the follicle progenitor cells can be obtained from a scalp biopsy of the patient in need of hair restoration, and the supplemental cells optionally also can be obtained from the patient. The use of these added cells, which produce important beneficial growth factors, obviates the need for or complements the effectiveness of the above mentioned growth factors. The endothelial cells, fat cells, and pre-adipocytes can be obtained from liposuction fat removed, for example, from the patient's abdominal fat and the bone marrow cells can be obtained, for example, by aspiration from the patient's hip bone.

The wounds in the desired implantation site may be made by any suitable technique. For example, the wounds may be made using a sharp instrument, such as a scalpel, trochar or needle, or the wounds may be made by a laser or by a punch. Suitably, the needle is an 18 or 19 gauge needle. The depth of the wound can be pre-determined by properly adjusting the protrusion length of a spear-point blade attached to a handle equipped with a threaded fastener made for this purpose. For example, SP90 and SP91 blades (Swarm-Morton Surgical, Sheffield, UK) with four sided spear-point tips were specially designed to allow control over depth and angle while creating recipient sites for hair follicle graft implantation.

A protectant may be placed in the wound prior to, during or following implantation of the hair graft. The term "protectant" refers to any substance of temporary duration that serves to protect the cells from trauma associated with implantation or destruction by the inflammatory process of wound healing. Many commercially and clinically available substances may be used as a protectant. Suitable protectants include, but are not limited to, collagen, hyaluronic acid, and chondroitin sulfate solutions. One suitable protectant is autologous serum from the subject in which the hair graft is implanted. Autologous serum may be obtained by drawing a small amount of whole blood from the subject and removing the cells by centrifugation. Advantages of using autologous serum include providing an anchor for the hair graft via natural clotting properties associated with the serum. Also, the autologous serum may contain nutrient molecules and other native beneficial factors to further nurture follicle neogenesis.

The grafts and methods of the present invention can be used to create new hair follicles and new hair on any region of the subject where new hair is desired. Suitably, the grafts and methods of the present invention are utilized to develop new hair on the scalp or eyebrow region of the subject. The subject may be any mammal. Suitably, the subject is a human.

It is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise. All publications, patents and patent applications referenced in this specification are indicative of the level of ordinary skill in the art to which this invention pertains. All publications, patents and patent applications are herein expressly incorporated by reference to the same extent as if each individual publication or patent application was specifically and individually indicated by reference. In case of conflict between the present disclosure and the incorporated patents, publications and references, the present disclosure should control.

It also is specifically understood that any numerical range recited herein includes all values from the lower value to the upper value, i.e., all possible combinations of numerical values between the lowest value and the highest value enumerated are to be considered to be expressly stated in this application. For example, if a concentration range is stated as 1% to 50%, it is intended that values such as 2% to 40%, 10% to 30%, or 1% to 3%, etc., are expressly enumerated in this specification.

The following examples are provided to assist in a further understanding of the invention. The particular materials, methods and conditions employed are intended to be illustrative of the invention and are not limiting upon the scope of the invention.

EXAMPLES

Example 1

Human dermal fibroblasts are obtained from newborn infant foreskin tissue and cultured. The cultured cells are seed on a bioabsorbable scaffold with a silicon rubber film backing. A piece of dorsal skin is excised from a nu/nu mouse without disturbing the underlying blood vessels. The seeded scaffold is implanted on the wound and the in situ blood supply maintains the viability of the seeded scaffold. After an appropriate healing time elapses, the silicone rubber backing is removed and hair follicle progenitor cells are delivered to the vascularized dermal tissue equivalent. The hair follicle progenitor cells are covered with an epidermal layer. The wound is allowed to heal and new hair follicles are formed.

Example 2

Human dermal fibroblasts and keratinocytes are obtained from newborn infant foreskin tissue and cultured according the procedures developed by Professors Auger and Germain (see, Pouliot, et al. in *Transplantation,* 2002 Jun. 15; 73(11): 1751-7, and referenced cited therein) to produce separate tissue engineered dermal and epidermal layers. A porous dermal regeneration template (5 mm thick) comprised of collagen and glycosaminoglycan, such as that sold by Integra Life Sciences, Inc. (Plainsboro, N.J.), is aseptically rinsed with sterile DMEM/F12 culture medium, and combined with the tissue engineered dermal layer and incubated in a cell culture incubator until the tissue engineered dermal layer and dermal regeneration template are attached. Dermal papilla cells are placed on top of the dermal layer and allowed to attach. The tissue engineered epidermal layer comprised of a sheet of keratinocytes is carefully transferred onto the papilla cell-seeded dermal tissue to complete the assembly of tissue engineered dermal layer and epidermal layer with dermal papilla cells sandwiched in between. This construct is cultured further until it possesses sufficient integrity, and then it is cultured with the epidermal layer exposed to air to induce the formation of mature skin according to standard procedure. The construct is than transported into the operating room where the patient is anesthetized and the surgeon creates recipient sites for the grafts with a spear-point blade, as is traditionally done with current follicle transplantation. Meanwhile, the technicians working with appropriate magnification and surgical tools cut the tissue engineered construct into "slivers" that are approximately 1 to 2 mm wide and are made by slicing the epidermal surface down to the bottom of the scaffold. The slivers are then cut into 1 to 2 mm wide pieces to produce graft that are typically 1×1×5 mm. These grafts are then loaded into the Choi implanter comprising a tube and push rod assembly. The graft goes in "head first" such that the epidermal surface is in contact with the push rod and the bottom of the scaffold is at the open end of the tube. The technician then inserts the tube into the recipient site and removes the tube while pushing on the push rod to deposit the graft exactly as planned by the surgeon. A properly implanted graft will have its epidermal layer in contact with the surrounding epidermis and the bottom of the scaffold will be at the level of the subcutaneous fat. The follicle neogenesis process initiated in vitro will continue in vivo such that new hairs will become visible at the implant sites within 3 to 6 months.

Example 3

A tissue engineered graft is prepared and implanted as described in Example 2 except that pre-adipocytes and vascular endothelial cells are added to the porous scaffold just prior to combination with the tissue engineered dermal layer. All other steps are as described above.

Example 4

A tissue engineered graft is prepared and implanted as described in Example 2 except that the scaffold is first coated with a solution of human collagen dissolved in 0.005M acetic acid and then is soaked and rinsed with buffered culture medium to insolubilize the collagen. Human foreskin fibroblasts are then seeded directly on the collagen coated scaffold and cultured until a tissue engineered dermal layer forms. The subsequent steps of seeding with papilla cells and layering with an epidermal sheet of keratinocytes are performed as previously stated.

What is claimed is:

1. A method of making a hair graft, comprising: a) incubating a tissue engineered dermal layer on a bioabsorbable scaffold until the tissue engineered dermal layer attaches to the bioabsorable scaffold; b) placing hair follicle progenitor cells on the tissue engineered dermal layer; c) placing a tissue engineered epidermal layer comprising a sheet of keratinocytes on the hair follicle progenitor cells to form a construct; d) allowing the construct to mature in vitro; and e) cutting the construct into one or more implantable grafts.

2. A method of implanting a hair graft comprising creating a wound in skin of a subject and implanting the graft of claim 1 into the wound, wherein the graft is at least about 2 millimeters thick.

3. The method of claim 1, wherein the tissue engineered dermal layer comprises human dermal fibroblasts.

4. The method of claim 1, wherein the hair follicle progenitor cells are selected from the group consisting of mesenchymal stem cells, dermal papilla cells, dermal sheath cells, and follicular epidermal stem cells.

5. The method of claim 1, wherein the tissue engineered epidermal layer comprises human epidermal keratinocytes.

6. The method of claim 1, wherein the bioabsorbable scaffold comprises collagen and glycosaminoglycan.

7. The method of claim 1, wherein the bioabsorbable scaffold comprises one or more moieties selected from the group consisting of a growth factor, an angiogenesis factor, a cell attachment binding site moiety, a cell signaling molecule, a polypeptide, a glycoprotein, and a bioactive molecule.

8. The method of claim 1, wherein one or more cells types selected from the group consisting of fat cells, pre-adipocytes, vascular endothelial cells, and bone marrow cells are added to the bioabsorbable scaffold prior to incubating the tissue engineered dermal layer with the bioabsorbable scaffold.

9. The method of claim 1, wherein the implantable grafts are about 1 to about 9 square millimeters in surface area.

10. The method of claim 1 wherein the tissue engineered dermal layer is a sheet of dermal cells.

11. The method of claim 1 wherein the bioabsorbable scaffold comprises a layer of collagen onto which the tissue engineered dermal layer is seeded and cultured to form a sheet prior to hair follicle progenitor cells on the tissue engineered dermal layer.

12. The method of claim 1 wherein the hair follicle progenitor cells are aggregated or clumped together prior to placement on the dermal layer.

13. The method of claim 12 wherein the size of the aggregates or clumps is 10 to 500 microns.

14. The method of claim 13 wherein the size of the aggregates or clumps is 20 to 200 microns.

15. The method of claim 14 wherein the size of the aggregates or clumps is 30 to 60 microns.

16. The method of claim 10 wherein the sheet of dermal cells and the sheet of keratinocytes are prepared separately by culturing isolated cells in vitro without the use of a scaffold.

17. The method of claim 1 wherein the construct is allowed to mature in vitro until the follicle neogenesis process is initiated.

* * * * *

UNITED STATES PATENT AND TRADEMARK OFFICE
CERTIFICATE OF CORRECTION

| | | |
|---|---|---|
| PATENT NO. | : 9,023,380 B2 | Page 1 of 1 |
| APPLICATION NO. | : 12/729700 | |
| DATED | : May 5, 2015 | |
| INVENTOR(S) | : Thomas H. Barrows et al. | |

It is certified that error appears in the above-identified patent and that said Letters Patent is hereby corrected as shown below:

Specification,
Column 1, line 10, replace "referenced" with --reference--.
Column 6, line 32, replace "seed" with --seeded--.
Column 6, line 46, replace "according the procedures" with --according to the procedures--.
Column 6, line 65, replace "is than transported" with --is then transported--.
Column 7, line 7, replace "to produce graft" with --to produce grafts--.

Claims,
Claim 1, column 7, line 43, replace "bioabsorable" with --bioabsorbable--.
Claim 8, column 8, line 19, replace "cells types" with --cell types--.

Signed and Sealed this
Twenty-seventh Day of October, 2015

Michelle K. Lee
*Director of the United States Patent and Trademark Office*